(12) United States Patent
Comin et al.

(10) Patent No.: US 8,781,754 B2
(45) Date of Patent: Jul. 15, 2014

(54) METHOD AND APPARATUS FOR DETECTING CONSENSUS MOTIFS IN DATA SEQUENCES

(75) Inventors: Matteo Comin, Venice (IT); Laxmi P. Parida, Mohegan Lake, NY (US)

(73) Assignee: International Business Machines Corporation, Armonk, NY (US)

( * ) Notice: Subject to any disclaimer, the term of this patent is extended or adjusted under 35 U.S.C. 154(b) by 1530 days.

(21) Appl. No.: 11/621,591

(22) Filed: Jan. 10, 2007

(65) Prior Publication Data

US 2008/0167850 A1     Jul. 10, 2008

(51) Int. Cl.
*G06F 19/00* (2011.01)
*G11C 17/00* (2006.01)
*G06F 15/00* (2006.01)
*G06F 19/22* (2011.01)

(52) U.S. Cl.
CPC .................................. *G06F 19/22* (2013.01)
USPC .................................. 702/20; 365/94; 700/1

(58) Field of Classification Search
CPC ......... G06F 19/22; G06F 19/16; G06F 19/18; G06F 19/24
See application file for complete search history.

(56) References Cited

U.S. PATENT DOCUMENTS

| 6,571,230 B1 | 5/2003 | Parida |
| 2004/0204925 A1 | 10/2004 | Alon et al. |

OTHER PUBLICATIONS

Berezikov et al. CONREAL: Conserved Regulatory Elements Anchored Alignment Algorithm for Identification of Transcription Factor Binding Sites by Phylogenetic Footprinitng Genome Research vol. 14, pp. 170-178 (2004).*
Schneider et al. Sequence logos: a new way to display consensus sequences Nucleic Acids Research vol. 18, pp. 6097-6100 (1990).*
Wang et al. Combining the phylogenetic data with co-regulated genes to identify regulatory motifs. Bioinformatics vol. 19, pp. 2369-2380 (2003).*
M.S. Waterman, R. Aratia, and D.J. Galas, "Pattern recognition in Several Sequences: Consensus and Alignment". Bulletin of Mathematical Biology, 46(4):515 {527, 1984).
M. F. Sagot, "Spelling Approximate Repeated or Common Motifs Using a Suffix Tree", Latin 98: Theoretical Informatics, Lecture Notes in Computer Science, 1380:111-127, 1998.
P.A. Pevzner and S.-H. Sze, "Combinatorial Approaches to Finding Subtle Signals in DNA Sequences", In Proceedings of the Eighth International Conference on Intelligent Systems for Molecular Biology, pp. 269-278, AAAI Press, 2000.
Buhler and Tompa, "Finding Motifs Using Random Projections", In Proceedings of the Annual Conference on Computational Molecular Biology, (RECOMB01), pp. 69-75, ACM Press, 2001.
Comin and Panda, "Subtle Motif Discovery for Detection of DNA Regulatory Sites", Proceedings Trim Size: 9.75in×6.5 in; pp. 1-10; Oct. 6, 2006.

* cited by examiner

*Primary Examiner* — John S Brusca
(74) *Attorney, Agent, or Firm* — Scully, Scott, Murphy & Presser, PC; Vazken Alexanian (57) ABSTRACT

Disclosed are a method of and system for detecting a consensus motif in a data sequence. The method comprises the steps of obtaining the data sequence, identifying potential signal (PS) segments of interest in the data sequence, and carrying out comparison and alignment processes amongst the PS segments to extract the consensus motif. Preferably, an unsupervised motif discovery process is used to identify the PS segments. More specifically, this may be done by extracting all common motifs across the sequence using the unsupervised motif discovery process; and for each of at least selected positions in the sequence, computing the weighted sum of the common motifs that cover said position. The PS segments that cover the positions where said number is above a given threshold may then be identified as the PS segments.

19 Claims, 4 Drawing Sheets

FOR $t = 20, l = 20$, THE EXPECTED NUMBER OF MAXIMAL MOTIFS $E(Z_{K,q})$, IS PLOTTED AGAINST QUORUM $K$ SHOWN ALONG THE X-AXIS, FOR DIFFERENT VALUES OF $q$.

FIG. 3

FOR $t = 20, l = 20$, THE EXPECTED NUMBER OF MAXIMAL MOTIFS $E(Z_{K,q})$, IS PLOTTED AGAINST QUORUM $K$ SHOWN ALONG THE X-AXIS, FOR DIFFERENT VALUES OF $q$, IN A LOGARITHMIC SCALE. NOTICE THAT WHEN $q = 1$, THE CURVE IS A HORIZONTAL LINE AT $y = 1$.

| MOTIF PARAMETERS | ALL MOTIFS | IRREDUNDANT MOTIFS |
|---|---|---|
| K20D2 | 2 | 3 |
| K19D2 | 0 | 1 |
| K20D3 | 3 | 4 |
| K19D3 | 1 | 2 |
| K20D4 | 2 | 5 |

NUMBER OF POSITIONS PREDICTED CORRECTLY USING ALL MOTIFS COMPARED WITH A *BASIS*, FOR THE $l = 15, d = 4, t = 20, n = 600$ CASE USING MOTIF DISCOVERY WITH QUORUM $K$ AND $D$ ERRORS. NOTE THAT $q = 11/15 \approx 0.73$

| MOTIF PARAMETERS | $N$ | SCORE | SC | $N$ | SCORE | SC |
|---|---|---|---|---|---|---|
| K20D1 | 2 | 0.038 | 10 | 2 | 0.066 | 10 |
| K20D2 | 2 | 0.003 | 10 | 2 | 0.415 | 12 |
| K20D3 | 3 | 0 | 9 | 4 | 1 | 20 |
| K20D4 | 4 | 0.88 | 20 | 3 | 1 | 20 |

(a) $l = 15, d = 4$

| MOTIF PARAMETERS | $N$ | SCORE | SC |
|---|---|---|---|
| K20D0 | 0 | 0.02 | 10 |
| K20D1 | 1 | 0.49 | 11 |
| K20D2 | 1 | 1 | 20 |
| K20D3 | 1 | 1 | 20 |
| K20D4 | 2 | 1 | 20 |

(b) $l = 17, d = 5$

THE MOTIF PARAMETERS ARE QUORUM $K$ AND $D$ ERRORS, $N$ IS THE TOTAL SIZE OF THE PS SEGMENTS PREDICTED CORRECTLY AND SC IS THE SOLUTION COVERAGE. THE NUMBER OF POSITIONS PREDICTED CORRECTLY FOR IN 20 SEQUENCES OF LENGTH 600 BASES EACH, WITH PLANTED MOTIF PARAMETERS AS SHOWN.

| MOTIF PARAMETERS | M | I | II |
|---|---|---|---|
| K10D2 | 95 | 8 | 7 |
| K9D2 | 236 | 8 | 10 |
| K8D2 | 434 | 7 | 8 |

(b) $n = 200, t = 20$

| MOTIF PARAMETERS | M | I | II |
|---|---|---|---|
| K20D2 | 281 | 10 | 10 |
| K19D2 | 459 | 12 | 13 |
| K18D2 | 588 | 18 | 18 |

(c) $n = 300$ $t = 20, l = 15, d = 4$

| MOTIF PARAMETERS | M | I | II |
|---|---|---|---|
| K20D2 | 539 | 2 | 4 |
| K19D2 | 647 | 6 | 7 |
| K18D2 | 837 | 12 | 12 |
| K17D2 | 1139 | 8 | 8 |
| K16D2 | 2056 | 9 | 9 |
| K20D3 | 952 | 5 | 6 |
| K19D3 | 1164 | 11 | 10 |
| K18D3 | 1582 | 13 | 13 |
| K17D3 | 2511 | 13 | 13 |
| K16D3 | 4432 | 13 | 13 |
| K20D4 | 1454 | 8 | 9 |
| K19D4 | 1832 | 9 | 10 |
| K18D4 | 2577 | 11 | 11 |
| K17D4 | 4055 | 12 | 12 |
| K16D4 | 7958 | 10 | 10 |

(d) $n = 400$

| MOTIF PARAMETERS | M | I | II |
|---|---|---|---|
| K20D2 | 1588 | 2 | 2 |
| K19D2 | 3526 | 1 | 1 |
| K18D2 | 5456 | 1 | 1 |
| K17D2 | 6607 | 0 | 0 |
| K16D2 | 7316 | 1 | 2 |
| K20D3 | 3348 | 4 | 4 |
| K19D3 | 7885 | 2 | 2 |
| K18D3 | 12444 | 1 | 1 |
| K17D3 | 15318 | 2 | 3 |
| K16D3 | 17017 | 0 | 1 |

THE TWO TABLES SHOW THE NUMBER OF PS SEGMENT POSITIONS PREDICTED CORRECTLY OF METHOD I WHICH DOES NOT USE STATISTICAL PRUNING AND METHOD II WHICH DOES. $M$ IS THE TOTAL NUMBER OF IRREDUNDANT MOTIFS DISCOVERED IN THE INPUT. THE MOTIF PARAMETER $K$ IS THE QUORUM AND $D$ IS THE NUMBER OR ERRORS. THE VALUES OF $q$, OBTAINED USING EQUATION 3, ARE AS FOLLOWS: (a) AND (b) $q = 0.8$, (c) AND (d) $q = 0.73$

METHOD AND APPARATUS FOR DETECTING CONSENSUS MOTIFS IN DATA SEQUENCES

BACKGROUND OF THE INVENTION

1. Field of the Invention

The present invention generally relates to data sequence processing methodologies, and more particularly, to methods and apparatus for detecting consensus motifs in sequences of data such as, for example, sequences of characters, character sets and real numbers.

2. Background Art

Given an input sequence of data, a "motif" is a repeating pattern, possibly interspersed with don't-care characters, that occurs in the sequence. The data could be characters or sets of characters or real values. In the first two cases, the number of motifs could potentially be exponential in the size of the input sequence and in the third case there could be uncountably infinite number of motifs. Typically, the higher the self-similarity in the sequence, the greater is the number of motifs in the data. Motif discovery on such data, such as repeating DNA or protein sequences, is a source of concern since such data exhibits a very high degree of self-similarity (repeating patterns).

At the same time, the problem of detecting common motifs across DNA sequences for locating regulatory sites, transcription binding factors or even drug target binding sites is of prime importance. The main difficulty is that these motifs have subtle variations at each occurrence. This problem has been of interest to both biologists and computer scientists. A satisfactory practical solution has been elusive although the problem is defined very precisely:

Problem 1 (The Consensus Motif Problem): Given t sequence $s_i$ on some alphabet $\Sigma$, a length $l>0$ and a distance $d \geq 0$, the task is to find all patterns p, of length l that occur in each $s_i$ such that each occurrence $p'_i$ on $s_i$ has at most d mismatches with p.

The problem in this form made its first appearance in 1984 (M. S. Waterman, R. Aratia, and D. J. Galas. Pattern recognition in several sequences: Consensus and alignment. *Bulletin of Mathematical Biology*, 46(4):515{527, 1984). In this discussion, the alphabet $\Sigma$ is {A, C, G, T} and the problem is made difficult by the fact that each occurrence of the pattern p may differ in some d positions and the occurrence of the consensus pattern p may not have d=0 in any of the sequences. In the above-mentioned paper, M. S. Waterman, R. Aratia, and D. J. Galas. Pattern recognition in several sequences: Consensus and alignment. *Bulletin of Mathematical Biology*, 46(4):515{527, 1984, Waterman and coauthors provide exact solutions to this problem by enumerating neighborhood patterns, i.e., patterns that are at most d Hamming distance from a candidate pattern. Sagot gives a good summary of the (computational) efforts in M. F. Sagot, "Spelling approximate repeated or common motifs using a suffix tree. *Latin 98: Theoretical Informatics, Lecture Notes in Computer Science*, 1380:111-127, 1998 and offers a solution that improves the time complexity of the earlier algorithms by the use of generalized suffix trees. These clever enumeration schemes, though exact, have a drawback that they run in time exponential in the pattern length.

This problem of detecting common subtle patterns across sequences is nevertheless of great interest and various statistical and machine learning approaches, which are inexact but more efficient, have been proposed. One of the questions that can be asked to compare and test the efficacy of such methods of consensus motif detection systems is: Given a set of sequences that harbor (with mutations) k motifs, what percentage of the k motifs does the system recover? When k is large, many approaches are known that give good average-case performance under this criterion.

Yet another question to ask is: Given a set of sequences that harbor (with mutations) ONE motif p, does the system recover p? This is a rather difficult criterion to meet since these algorithms use some form of local search based on Gibbs sampling or expectation maximization or even clever heuristics. Hence it is not surprising that they may miss p. However, a question of this form is a biological reality. Consider the following, somewhat contrived, variation of Problem 1 which is an attempt at simplifying the computational problem.

Problem 2 (The Planted (l, d)-motif problem): Given t sequence $s'_i$ on $\Sigma$, a pattern p of length l is embedded in $s'_i$, with exactly d errors (mutations), to obtain the sequence $s_i$ of length n, for each $1 \leq i \leq t$. The task is to recover p, given $s_i$, $1 \leq i \leq t$ and the two numbers l and d.

Pevzner and Sze set forth the challenge problem, which was Problem 2 with parameters n=600, t=20, l=15 and d=4 (P. A. Pevzner and S.-H. Sze, "Combinatorial approaches to finding subtle signals in DNA sequences", In *Proceedings of the Eighth International Conference on Intelligent Systems for Molecular Biology*, Pages 269-278, AAAI Press, 2000). There also is a need for the deployment of combinatorial approaches to tackle this problem. One of the algorithms they presented was an exact algorithm, where the challenge problem was reduced to finding a t-sized clique in a t-partite graph with at most n−l+1 vertices in each partition. Even the best-known heuristics for clique finding problem failed to detect the clique corresponding to the signal. The second algorithm was based on enumerating possible patterns and checking their candidacy for being the subtle pattern using clever heuristics and an exhaustive search in a reduced space.

One effective algorithm is the one discussed by Buhler and Tompa, "Finding motifs using random projections", In *Proceedings of the Annual Conference on Computational Molecular Biology*, (RECOMB01), Pages 69-75, ACM Press, 2001. The probabilistic algorithm uses a random projection h and hashes each input l-mer x into bucket h(x). Any hash bucket with sufficiently many entries is explored as a potential embedded motif. This approach solved the challenge problem and some more.

SUMMARY OF THE INVENTION

An object of this invention is to detect consensus motifs that occur with subtle variations across multiple sequences.

Another object of the invention is to detect a consensus motif in a group of sequences by first identifying potential signal segments of interest in the sequences, and then, amongst these segments, carrying out comparison and alignment processes to extract the consensus motif.

These and other objectives are attained with a method of and system for detecting a consensus motif in a data sequence. The method comprises the steps of obtaining the data sequence, identifying potential signal (PS) segments of interest in the data sequence, and carrying out comparison and alignment processes amongst the PS segments to extract the consensus motif. Preferably, an unsupervised motif discovery process is used to identify the PS segments. More specifically, this may be done by extracting all common motifs across the sequence using the unsupervised motif discovery process; and for each of at least selected positions in the sequence, counting the number of, or computing the weighted sum of, the common motifs that cover said position.

The PS segments that cover the positions where said number is above a given threshold may then be identified as the PS segments.

A central goal of the present invention is to detect the consensus or the embedded or the planted motif in the given data sets, which is also sometimes referred to as the signal in the data or the subtle signal. When a motif is not qualified with these terms, it refers to a substring that appears in multiple sequences, with possible wild cards.

The preferred embodiment of the present invention utilizes an approach that uses unsupervised motif discovery to solve Problem 2. This method works well for the more general Problem 1 as well. Recall that the signal ("subtle motifs") is embedded in t random sequences. The problem is compounded by the fact that although the consensus motif is solid (i.e., an l-mer without wild cards or dont-care characters), it is not necessarily contained in any of the t sequences. However, if we can obtain a correct alignment of the m sequences, then it is relatively easy to extract the consensus motif satisfying the (l, d) constraint. In other words, one of the difficulties of the problem is that the sequences are unaligned. The extent of similarity across the sequences is so little that any global alignment scheme cannot be employed. So we tackle this problem in two steps: First, we identify potential signal (PS) segments of interest in the input sequences. This is done by using the imprints of the discovered motifs on the input. Second, amongst these segments, we carry out an exhaustive comparison and alignment to extract the consensus motif.

Thus the main focus of our method is in obtaining good quality PS segments and restricting the number of such segments to keep the problem tractable. The Type I error or false negative errors, in detecting PS segments, are reduced by using appropriate parameters for the discovery process based on a careful statistical analysis of consensus motifs. The type II error or false positive errors are reduced by using irredundant motifs (A. Apostolico and L. Parida, "Incremental paradigms for motif discovery", *Journal of Computational Biology*", 11(4):15-25, 2004) and their statistical significance measures (A. Apostolico, M. Comin, and L. Parida, "Conservative extraction of over-represented extensible motifs", *ISMB (Supplement of Bioinformatics)*, 21:9-18, 2005). Generally speaking, the former helps to control the extent of over-counting of patterns and the latter helps filter the true signal from the signal-like-background.

The delineation into two steps helps us also address a more realistic version of the problem that includes insertion and deletion in the consensus motif:

Problem 3 (The Indel Consensus Motif Problem): Given t sequence $s_i$ on some alphabet $\Sigma$, a length $l>0$ and a distance $d\geq0$, the task is to find all patterns p, of length l that occur in each $s_i$ such that each occurrence $p'_i$ on $s_i$ is at an edit distance (mutation, insertion, deletion) at most d from p.

Here the unsupervised discovery process detects extensible motifs (instead of rigid motifs that have a fixed imprint length in all the occurrences). Also, the second step takes possible gaps in the alignment process.

Further benefits and advantages of this invention will become apparent from a consideration of the following detailed description, given with reference to the accompanying drawings, which specify and show preferred embodiments of the invention.

DETAILED DESCRIPTION OF THE PREFERRED EMBODIMENTS

Figure 1:
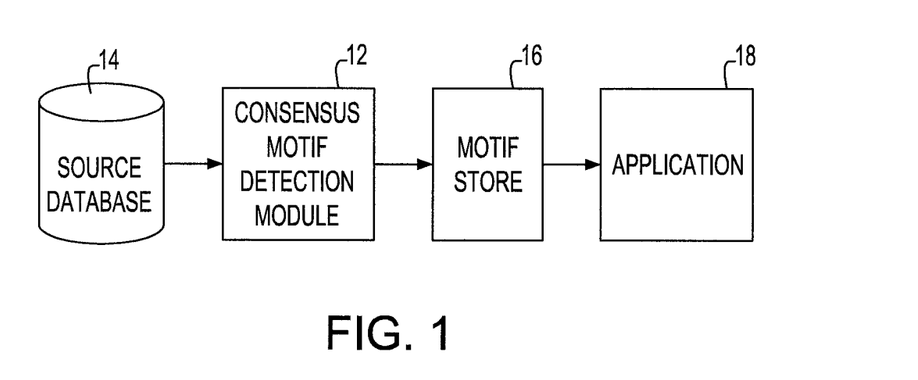
FIG. 1 is a block diagram illustrating a motif discovery and generation system according to one embodiment of the present invention.

Referring initially to FIG. 1, a block diagram of a motif detecting system according to an embodiment of the present invention is shown. The illustrative system 10 includes a motif detection module 12, a source sequence database 14 and a motif store 16. Also shown is an application 18, which is not necessarily part of the system, but which utilizes one or more of the motifs stored in store 16. Generally, the module 12 employs a pattern discovery or detection algorithm, to be explained in detail below, in order to discover consensus motifs from data input from a source database 14. It is to be appreciated that the source database comprises data sequences from which repeating data patterns are discovered for use by one or more applications such as, for example, data mining, clustering or matching applications. The data sequences in the database may, for example, be in the form of sequences of discrete characters from a fixed character alphabet, sets of discrete characters from a fixed character alphabet, or sequences/sets of real numbers.

It is to be appreciated that another application, which may implement the motif detection methodologies of the invention, is deoxyribonucleic acid (DNA) or protein sequence homology detection. In such an application, a probe protein sequence may be submitted to a search engine system implementing the invention in order to check for k occurrences of the probe sequence in the database of protein sequences.

Figure 2:
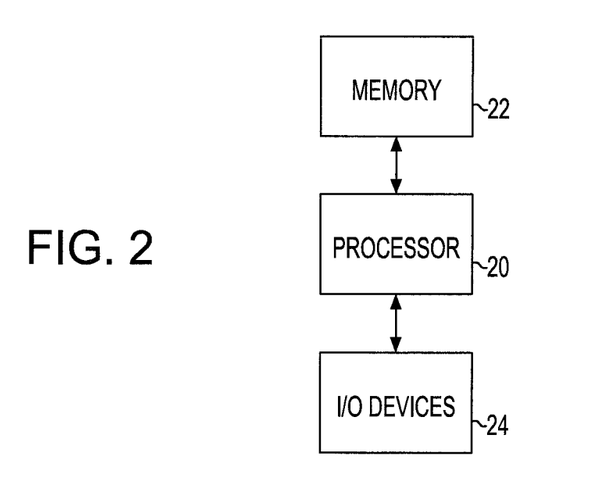
FIG. 2 is a block diagram illustrating a hardware implementation of a motif discovery and generation system according to one embodiment of the present invention.

FIG. 2 is a block diagram of an exemplary hardware implementation of the system 10 of FIG. 1. As shown, the system 10 may be implemented in accordance with a processor 20 a memory 22 and I/O devices 24. It is to be appreciated that the term "processor" as used herein is intended to include any processing device, such as, for example, one that includes a CPU (central processing unit). The term "memory" as used herein is intended to include memory associated with a processor or CPU, such as, for example, RAM, ROM, a fixed memory device (e.g., hard drive), a removable memory device (e.g., diskette), flash memory, etc. In addition, the term "input/output devices" or "I/O devices" as used herein is intended to include, for example, one or more input devices, e.g., keyboard, for entering sequences and/or other data to the processing unit, and/or one or more output devices, e.g., CRT display and/or printer, for presenting discovery results and/or other results associated with the processing unit. It is also to be understood that the term "processor" may refer to more than one processing device and that various elements associated with a processing device may be shared by other processing devices. Accordingly, software components including instructions or code for performing the methodologies of the invention, as described herein, may be stored in one or more of the associated memory devices (e.g., ROM, fixed or removable memory) and, when ready to be utilized, loaded in part or in whole (e.g., into RAM) and executed by a CPU.

It is to be appreciated that, in an alternative embodiment, the invention may be implemented in a network-based implementation. That is the user may submit source data sequences (in lieu of a separately stored source database 14) at a remote client computer system, while the detection module 12 resides and is executed on a server computer system in communications with the client via a network such as, for example, the Internet. The network could alternatively be a private network and/or a local network. Thus, a user operating remotely on his client computer system, e.g., a personal computer, laptop and/or some other type of personal processing device, enters data sequences through application software running on the computer system, e.g., web browsing software and/or a graphical user interface associated with the system. The sequences are passed over the network, in a conventional manner, and processed by server. The server receives the sequences and executes the methodologies of the invention in order to discover and/or generate motifs. The server then returns some or all of the results to the client via the network. It is to be understood that the server may include more than one computer system. That is, one or more of the elements in FIG. 2 may reside on and be executed by their own computer system, e.g., with its own processor, memory and I/O devices. Given a general description of the elements of the motif discovery system of the invention and various exemplary hardware implementations, the various inventive methodologies will now be explained in detail.

For ease of reference, the remainder of the detailed description is divided into sections as follows: (I) Statistics of consensus motifs; (II) The Preferred Approach Of This Invention; and (III) Results Achieved With The Preferred Embodiment of the Invention.

I. Statistics of Consensus Motifs

We consider the most general version of the problem, which is formally stated above as Problem 3. Recall that this setting permits insertion and deletion as well as mutation in the embedded motif.

Given t sequences of length l each, a pattern satisfies quorum K if it occurs in K'≥K of the given t sequences. Further it is of maximal size h, if in each of the K' occurrences, the size cannot be increased without decreasing the number of occurrences K'.

For simplicity, the sequences are the same length l as the consensus motif and all the t sequences are aligned and we will further assume that a pattern occurs at most once in each sequence. Let q be the probability of any position in the input data to be contained in a pattern and let $P_{maximal}(K, H, q)$ be the probability that a pattern with maximal H solid characters and quorum K occurs in the input data. Then, $$P_{maximal}(K, H, q) = \sum_{k=K}^{t} \binom{t}{k}(1-q^H)^{t-k} q^{Hk}(1-q^k)^{l-H} \quad (1)$$

Let $Z_{K,q}$ be a random variable denoting the number of maximal motifs with quorum K and q as defined above, and, $E(Z_{K,q})$ denotes the expectation of $Z_{K,q}$. Note that for maximal motifs, it is the case that the occurrences of two distinct motifs are independent events. Further, using linearity of expectations, we obtain, $$E(Z_{K,q}) = \sum_{h=1}^{l} \binom{l}{h} P_{maximal}(K, H, q) \quad (2)$$

Computing q. Consider the case where the embedded motif is constructed with some d edit operations. Let the edit operations be (1) mutation, (2) deletion and (3) insertion. Let $q_M$ be the probability of mutation, $q_X$ the probability of deletion and $q_I$ the probability of insertion with $q_M+q_X+q_I=1$.

Note that for simplicity we have assumed that the t sequences are aligned. For example, the table on the left below shows exactly one edit applied to the signal motif and the table on the right shows the alignment of the embedded motifs.

| Edits | Signal = ACGTAC | | | | | | Alignment | | | | | |
|---|---|---|---|---|---|---|---|---|---|---|---|---|
| M | A | C | G | T | C | C | A | C | G | — | T | — | C |
| X | A | G | T | A | C | | A | — | G | — | T | A | C |
| I | A | C | G | A | T | A | C | A | C | G | — | T | A | C |
| M | A | C | C | T | A | C | A | C | — | — | T | A | C |
| M | G | C | G | T | A | C | — | C | G | — | T | A | C |

Assume that d out of the l positions are picked at random on the embedded motif for exactly one of the edit operations, insertion, deletion or mutation. Then it is easy to see that probability q of a position to be contained in a motif is:

$$q = 1 - \frac{d}{l}(q_M + q_X) \quad (3)$$

Now, it is straightforward to compute the value of q, to estimate $E(Z_{K,q})$ of Equation (2), given different scenarios. For example, consider the following cases.
(1) Exactly d mutations $q_M=1$ q=1−d/l
(2) Exactly d edits $q_M=q_X=q_I=\frac{1}{3}$ q=1−2d/3l
(3) Exactly d edits, $q_M=\frac{1}{2}$; $q_X=q_I=\frac{1}{4}$ q=1−3d=4l
    with equiprobable indel and mutation Also note that when no more than d0 edit operations are carried out on the embedded motif, it is usually interpreted as each collection of 0, 1, 2, . . . , d' positions being picked with equal probability, and thus d=d'/2 for Equation (3).

Rationale for Using Unsupervised Motif Discovery

Figure 3:
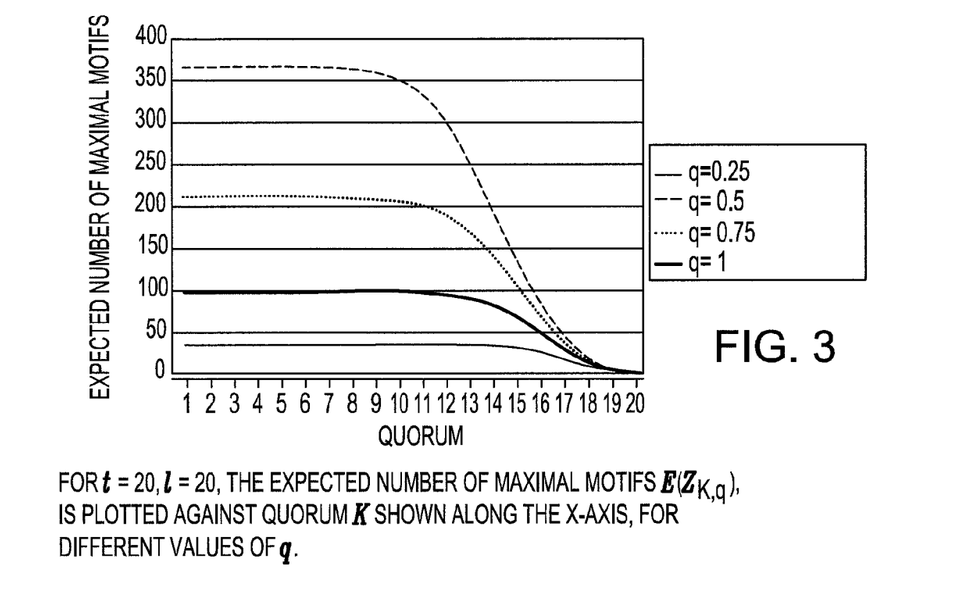
FIG. 3 shows, for a given set of conditions, the expected number of motifs in a given sequence.

A motif of length l that occurs across t'≤t sequences provides a local alignment of length l for the t' sequences which, in a sense, justifies the simplified scenario discussed above. The best-case scenario, for our problem, is when the embedded motif m is identical in all t sequences and the discovery process detects this single maximal motif with quorum t. So the scenarios closer to the best case should have fewer (but important) maximal motifs. FIG. 3 shows the expected number of motifs with different values of q and quorum K. Notice that the expected number of motifs remains the same for small values of K and falls dramatically as K increases.

The value of q is determined by the given problem scenario and thus a large value of K is a good handle on controlling the number and "quality" of maximal motifs.

The signal is embedded in the background and it is important to exploit the characteristics that distinguish one from the other. In our case, we assume that the background is random, in other words it is assumed to be randomly generated using an i.i.d process. Under this condition, it is easy to see that $q=\frac{1}{4}$. Thus we need to compare $E(Z_{K,q})$ with $E(Z_{K,1/4})$, the expectation for the random case. To compare these expectation curves, particularly around small values (close to 1 in the Y-axis), we study the plots of $\log(E(Z_{K,q}))$ against quorum K in FIG. 4.

Figure 4:
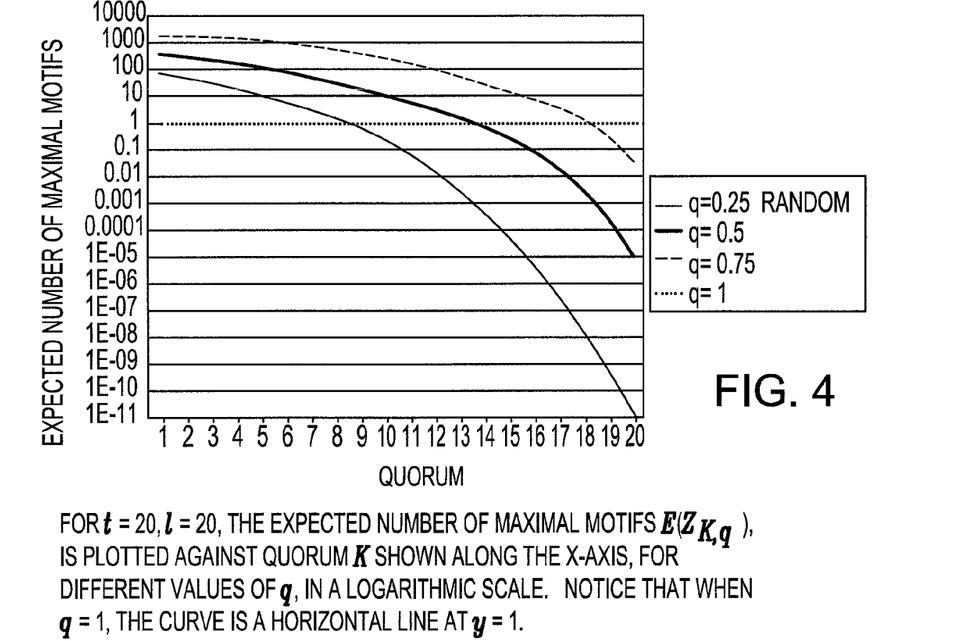
FIG. 4 shows the expected number of maximal motifs, for a given set of conditions, in a given sequence.

For example, consider the case when q=0.75. In FIG. 4, this is shown by the red curve and for large K, say K≥16, the expected number of motifs is small. Also, the corresponding expected numbers for the random case is extremely low, thus providing a strong contrast in the number of expected motifs. Hence the reasonable choice for the quorum parameter K is 16 or more, in the unsupervised discovery process.

It may be noted that in the case where the embedded motif is changed with insertions and/or deletions, the burden is heavier for the unsupervised discovery process and we use the extensible (or, variable-sized gaps) motif discovery algorithm, Varun (A. Apostolico, M. Comin, and L. Parida, "Conservative extraction of over-represented extensible motifs. *ISMB* (*Supplement of Bioinformatics*), 21:9-18, 2005).

II. The Preferred Approach of this Invention

The preferred approach of this invention is comprised of two main steps. We first locate regions in the sequence called potential signal (PS) segments. The statistical analysis of the previous section suggests that the detection of PS segments via unsupervised motif discovery is indeed possible. In the second step we align these short segments and extract the consensus motif.

Detecting PS Segments

As seen in the last section, in the range of an appropriate quorum K, we expect to see more maximal patterns in the signal region than the background. As the first approach, we extract all common motifs across sequences using an unsupervised motif discovery process. We use the system Varun (A. Apostolico, M. Comin, and L. Parida, "conservative extraction of over-represented extensible motifs", *ISMB* (*Supplement of Bioinformatics*), 21:9-18, 2005) for this purpose. This allows us to discover motifs with "dont-cares" or wild cards. The number of such characters is controlled by the parameter D in Varun. Next we simply count the number of motifs that cover a position i on the input. The first predictions of the PS segments are the positions with high counts (say the top 5%).

This elementary rule works well for simple cases like Problem 2 with n=600, t=20, l≤10 and d=2. Here the PS segments are predicted accurately. However, for d>2 we found that this simple approach is unable to distinguish between true and false PS segments. To weed out some of these wrong PS segments, we next explored some further combinatorial and statistical means of intelligently pruning the motifs. Firstly, we use the idea of irredundant or basis motifs (A. Apostolico and L. Parida, "Incremental paradigms for motif discovery", *Journal of Computational Biology*, 11(4):15-25, 2004), to avoid over counting of patterns that cover the same region multiple times on the sequence. Secondly, we consider only those motifs that have a significant z-score and further, bias the count with the probability of the occurrence of that motif.

It may be helpful, at this point, to review irredundancy and statistical significance of motifs.

Irredundancy and Statistical Significance of Motifs

Let s be a sequence from an alphabet $\Sigma \cup \{.\}$, where "." $\notin \Sigma$ denotes a don't care (dot, for short) and the rest are solid characters, we use a to denote a singleton character. For characters $e_1$ and $e_2$, we write $e_1 \preceq e_2$ if and only if $e_1$ is a dot or $e_1=e_2$. Allowing for spacers in a string is what makes it gapped. A dot character indicates such spacers. Whenever defined, d will denote the maximum number of consecutive dots allowed in a string. A string m occurs at position l on s if $m[j] \preceq s[l+j-1]$ holds for $1 \leq j \leq |m|$.

For a sequence s and positive integer k, k≤|s|, a string m is a motif of s with $|m|.>1$ and location list $L_m=(l_1, l_2, \ldots, l_p)$, if both m[1] and m[|m|] are solid and $L_m$ is the list of all and only the occurrences of m in s. Given a motif m let m[j1], m[j2], ... m[jl] be the l solid elements in the motif m. Then the sub-motifs of m are given as follows: for every $j_i$, $j_r$, the sub-motif $m[j_i \ldots j_r]$ is obtained by dropping all the elements before (to the left of) $j_i$ and all elements after (to the right of) $j_r$ in m. We also say that m is a condensation for any of its sub-motifs. We are interested in motifs for which any condensation would disrupt the list of occurrences. Formally, let $m_1, m_2, \ldots, m_k$ be the motifs in a string s. A motif $m_i$ is maximal in length if there exists no $m_j$, l≠i with $|L_{m_i}|=|L_{m_j}|$ and $m_i$ is a sub-motif of $m_j$. A motif $m_i$ is maximal in composition if no dot character of $m_i$ can be replaced by a solid character that appears in all the locations in $L_{m_i}$. A motif is called maximal if it is maximal in composition and in length.

Requiring maximality in composition and length limits the number of motifs that may be usefully extracted and accounted for in a string. However, the notion of maximality alone does not suffice to bound the number of such motifs. It can be shown that there are strings that have an unusually large number of maximal motifs without conveying extra information about the input.

A maximal motif m is irredundant if m and the list $L_m$ of its occurrences cannot be deduced by the union of a number of lists of other maximal motifs. Conversely, we call a motif m redundant if m (and its location list $L_m$) can be deduced from the other motifs without knowing the input string s. More formally:

Definition 1 (Redundant, Irredundant motif) A maximal motif m, with location list $L_m$, is redundant if there exist maximal sub-motifs $m_i$, 1≤i≤p, such that $L_m = L_{m_1} \cup L_{m_2} \ldots \cup L_{m_p}$ (i.e., every occurrence of m on s is already implied by one of the motifs $m_1, m_2, \ldots, m_p$). A maximal motif that is not redundant is called an irredundant motif.

Thus the set of irredundant motifs, denoted by B (also called the basis set), selects only those motifs that can describe the entire motif space. It also reduces the search space dimensionality from exponential to polynomial, without any loss of information. In particular if n is the length of the input string and k is the minimum quorum one can prove that if k=2 then $$|B| \leq n-1 \text{ and that in general } |B| \leq \binom{n-1}{k-1}.$$

Extensible Motifs

The motifs described above are also called rigid motifs. In other words, the length of the imprint of each occurrence of a motif is the same. However, we can define extensible motifs where this imprint length may change (in a controlled manner) at each occurrence. In other words, an extensible motifs is a concatenation of rigid strings (each with possible dot characters) and the gap between the rigid sections is denoted by a dash ('-') character, which represents up to d gaps in the imprint of each occurrence.

The above-mentioned paper "Incremental paradigms for mot discovery" shows show that given a string of length n and k=2, each element of the basis corresponds to an autocorrelation of the string and since there are no more than n autocorrelations, the size of the basis is no more than n. However, when the motifs are extensible, the picture is more complicated. Assume that a rigid segment of the motif must be of at least length r, then the number of autocorrelations is $O(n2^{(n/}$ $r$). It is unclear to us whether we can get a better bound on the size of the basis of extensible motifs.

Nevertheless, the use of irredundancy is useful even in extensible motifs, since repetitive motifs can be filtered without leading to over counts.

Statistical Significance of Motifs

When the alphabet size $|\Sigma| \ll n$, the chances of finding recurring motifs even in random sequences increase dramatically. Thus after the "combinatorial" elimination of candidate motifs, using quorum, density parameters (d) and irredundancy, we also use "statistical" elimination using z-scores.

An extensible motif is degenerate if it can possibly have multiple occurrences at a site i on the input s. Let m be an extensible non-degenerate motif generated by a stationary, i.i.d. source which emits ($\sigma \in \Sigma$) with probability $p_\sigma$. Let $j_\sigma$ be the number of times $\sigma$ appears in m and let e be the number of dash characters in m with gap sizes $\alpha_1, \alpha_2, \ldots \alpha_e$. Then $$Pm = \prod_{\sigma \in \Sigma} (p_\sigma)^{j_\sigma} \prod_{i=1}^{e} |\alpha_i| \quad (4)$$

Further, let $M^s$ denote a set of strings that has only the solid characters of at least s occurrences of m. For example, consider the motif a-b with realizations a.b, a..b and a...b. Then $M^1 = \{a.b, a..b, a...b\}$ since m occurs once on each $m \in M^1$; $M^2 = \{a.b, a..b, a...b\}$ since m occurs twice on each $m \in M^2$; $M^3 = \{a.bbb\}$ since m occurs three times on $m \in M^3$. Let m be a degenerate (possibly with multiple occurrences at a site) extensible motif, and let $p_m^k = \sum_{m' \in M^{k+1}} p_{m'}$, then $$p_m = \sum_{k=0}^{r-1} (-1)^k (p_m^{k+1}) \quad (5)$$

This follows directly from the inclusion-exclusion principle. Notice that for a degenerate motif, Equation (4) is the zeroth order approximation of Equation (5). The first order approximation is $p_m \approx p_m^1 - p_m^2$ and the second order approximation is $p_m \approx p_m^1 - p_m^3$ and so on. Using Bonferroni's inequalities, a kth order approximation of $p_m$ is an over-estimate of $p_m$, if k is odd.

To summarize, if $p_m$ be the probability of the motif m occurring at any location i on the input string s with n=|s| and $k_m$ is the observed number of times it occurs on s and if it can be assumed that the occurrence of a motif m at a site is an i.i.d. process, then the z-score is given as:

$$\frac{k_m - np_m}{\sqrt{np_m(1-p_m)}} \quad (6)$$

Note that the redundant motifs are no more surprising, in terms of their z-score, than the irredundant motifs, thus allowing us to combine algorithmically irredundancy with z-scores.

Back to PS Segment Computation

Figure 5:
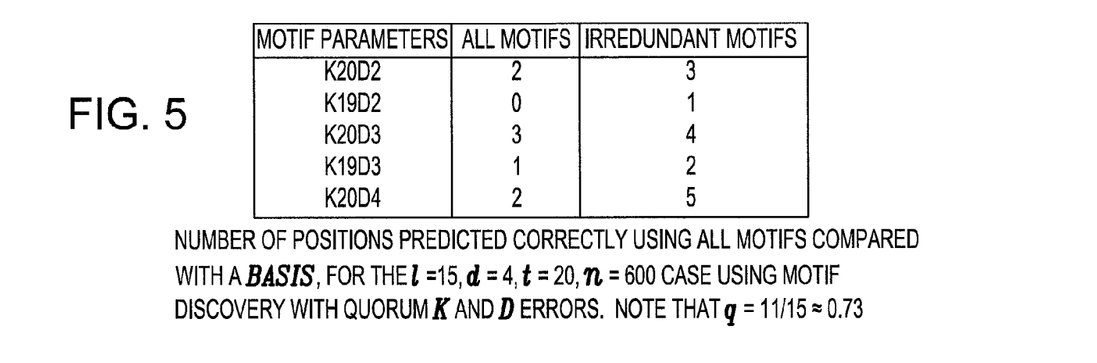
FIG. 5 shows a comparison of the number of correct potential signal (PS) segments with and without the use of irredundancy.

We use Varun to discover irredundant motifs in the input data. FIG. 5 shows a comparison of the number of correct PS segments with and without the use of irredundancy.

Figure 6:
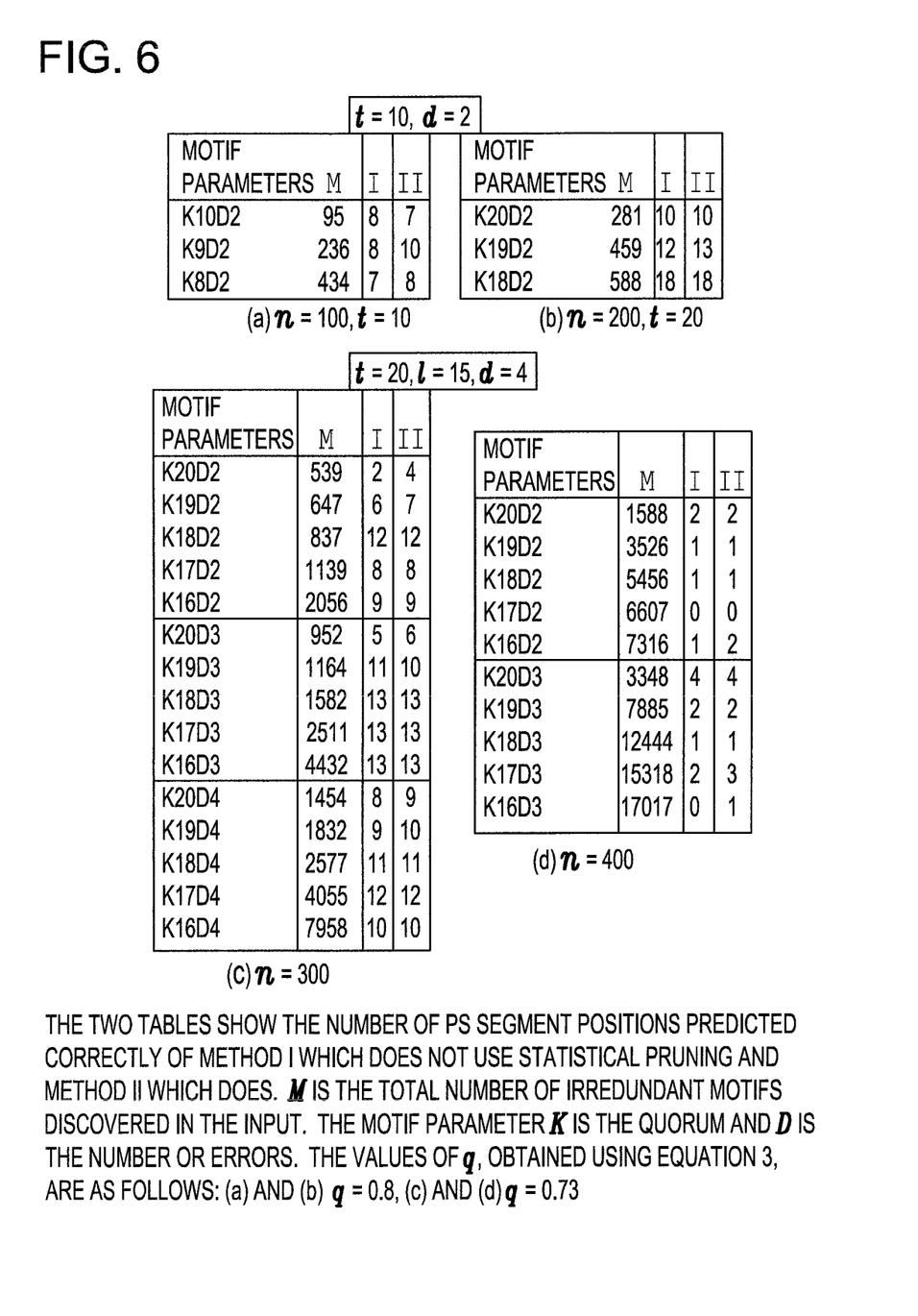
FIG. 6 includes two tables that show the number of PS segments predicted correctly using two different methods.

We compute the z-score of each irredundant motif using Equation (6) and filter these motifs based on a cut-off threshold z-score. We further use a weighted count for each input position in the imprint of the motif m, where the weight is $(1-p_m)$ and $p_m$ is computed as in Equation (5). FIG. 6 shows the results for a variety of settings comparing the use of statistical methods (both z-score and weighted counting), called Method II, with the one that does not use them, called Method I.

Notice that using the statistical pruning (Method II), we can restore all 10 positions of the n=200, t=20, l=10 and d=2 of Problem 2. However in our experiments, not surprisingly, we find that as n is increased, the number of correctly detected PS segments decreases. In particular, in the preliminary experiments for l=15 and d=4, we can recover 4 out of 20 correct positions. In most cases, the top positions, using Method II, are correct. In particular, with the best conditions we have, 5 correct predictions in the top 6 list and 7 in the first 9.

Since it is very difficult to detect 100% of the PS segments correctly in this step alone, we use these partial PS segments in the next step to reconstruct the true signal.

(Step 2) Processing PS Segments

In the last step we identified potential signal (PS) segments using the position space in each sequence. Next, we merge the information from each sequence by combining different PS segments. The basic idea is that if we assume that the PS segment is predicted correctly, then the planted motif is embedded in this segment. If the length of the consensus motif is known, say l, then the PS segment is constrained to be substring of length 2×l. Thus, given a candidate position i, the signal is contained in the interval [i−l, l+l].

We next need to pick one PS segment from each sequence to "locally align" the segments across the K(≤t) sequences. Let the K PS segments, each from a distinct sequence, be given as $(s_{i1}[b_{i1}, e_{i1}], s_{i2}[b_{i2}, e_{i2}], \ldots, s_{iK}[b_{iK}, e_{iK}])$. We make the assumption that the starting position $x_{ij}$ of the consensus motif in sequence $s_{ij}$ lies in the substring $s_{ij}[b_{ij}, e_{ij}]$, i.e., $b_{ij} \leq x_{ij} \leq e_{ij}$. We next use a simple measure to evaluate the alignment. The majority substring of length l, $s_m$ is simply the string obtained by using the majority base at each aligned position (column) and the score f is the sum total of positions in all the K segments that agree with $s_m$.

Recall that we need to pick only one PS segment from each sequence. We do this by enumerating all possible combinations. Since our first step is very tightly controlled, we found in practice that there are only a few candidate PS segments.

Also, in the model that uses insertion and deletion (i.e., the length of the imprint of the occurrence of the consensus motif in each sequence is not necessarily l), we use the same score by keeping track of the alignment columns: deletions and insertions result in gaps in some sequences in the alignment.

We consider all those alignments, whose score f exceeds a fixed threshold $T_K$. A small value of K reduces the number of positions that we need to consider, thus the computational time, and at the same time increases the chance of predicting K positions correctly. Note that the threshold $T_K$ is related to the size of the set K, in our experiments we use K=3 and we estimate the corresponding threshold from random samples to be $T_K$=33.

Extracting the Consensus Motif Across t Sequences

At the previous step, we have multiple alignments, where each alignment is across some K(<t) sequences. From these we need to extract the consensus motif across all the t sequences.

For each alignment, we compute a putative consensus motif by obtaining the majority substring $s_m$ (discussed above) and scan all the t input strings for the occurrence of $s_m$ with at most d errors. For each sequence, we pick the best occurrence, i.e., with the minimum edit distance from $s_m$. In practice, this step very quickly discards the erroneous consensus motifs and quickly converges to the one(s) satisfying the distance constraint of d.

III. Results

The result of detecting the embedded motif is either a success, or a failure. However, realistically it is better to have a measure that is more informative than just the two extreme values. Below we describe two reasonable measures and evaluate our experimental results with these two measures.

Let P be the set of all positions covered by the prediction and S be the same set for the embedded motif. The score of the prediction P, with respect to the embedded motif, can be given as:

$$score = \frac{|P \cap S|}{|P \cup S|}$$

Figure 7:
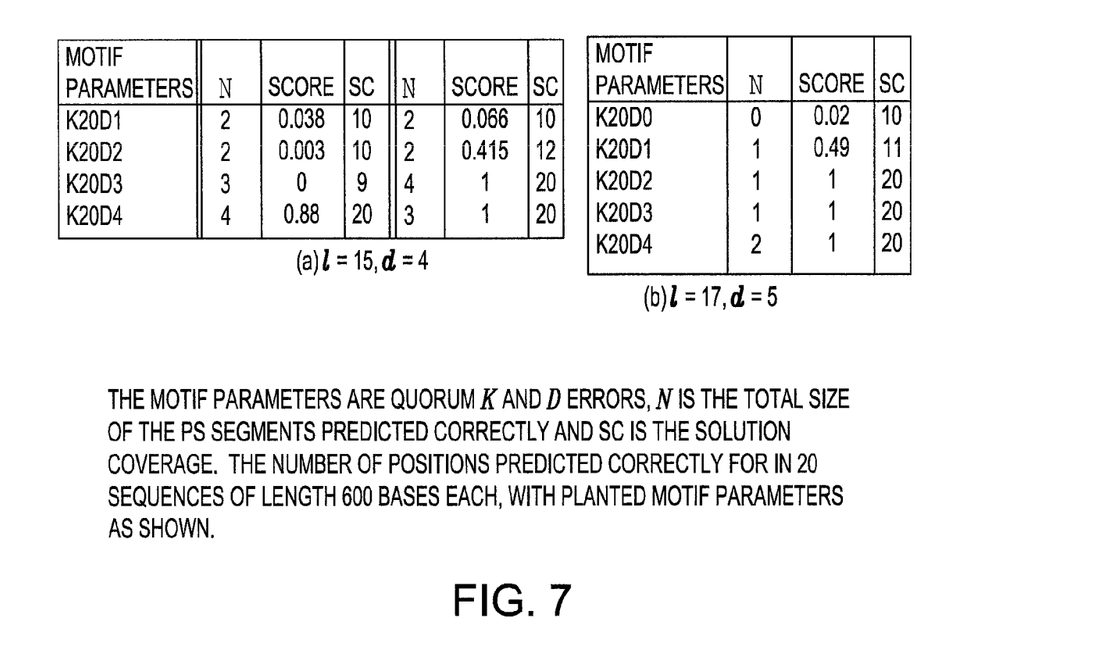
FIG. 7 shows a number of parameters, including the number of positions predicted correctly, obtained using the present invention.

The score is 1 if the prediction is 100% correct. However, even for values much smaller than 1, the embedded motif may be correctly predicted. This measure is rather stringent and yet another measure, the coverage score (CS), can be used. This is defined as the number of sequences that contains at least one occurrence of the predicted motif whose distance from the prediction is within the problem constraint i.e., bounded by d. Again if the coverage is equal to the total number of sequences t, then the prediction can be considered 100% correct. We report our results in terms of these two measures in FIG. 7 where the parameters chosen are the ones that are used by the community as benchmark data.

The problem of detecting subtle consensus motifs is difficult, and purely combinatorial or only statistical methods have been unsatisfactory. And, it appears it requires a delicate combination of the two. We have presented a method that uses unsupervised combinatorial pattern discovery, followed by a careful statistical refinement and processing. Since we use general tools such as pattern discovery, in the first step, and local alignment, in the second step, we have focused more on choosing and combining appropriate parameters. Also, extension of the method to handling a more general scenario such as inclusion of indels (insertion and/or deletion) in the embedded motif is relatively straightforward. We achieved this by using extensible motifs in the pattern discovery process of the first step and gapped alignment in the second step.

As will be readily apparent to those skilled in the art, the present invention can be realized in hardware, software, or a combination of hardware and software. Any kind of computer/server system(s)—or other apparatus adapted for carrying out the methods described herein—is suited. A typical combination of hardware and software could be a general-purpose computer system with a computer program that, when loaded and executed, carries out the respective methods described herein. Alternatively, a specific use computer, containing specialized hardware for carrying out one or more of the functional tasks of the invention, could be utilized.

The present invention, or aspects of the invention, can also be embodied in a computer program product, which comprises all the respective features enabling the implementation of the methods described herein, and which—when loaded in a computer system—is able to carry out these methods. Computer program, software program, program, or software, in the present context mean any expression, in any language, code or notation, of a set of instructions intended to cause a system having an information processing capability to perform a particular function either directly or after either or both of the following: (a) conversion to another language, code or notation; and/or (b) reproduction in a different material form.

While it is apparent that the invention herein disclosed is well calculated to fulfill the objects stated above, it will be appreciated that numerous modifications and embodiments may be devised by those skilled in the art, and it is intended that the appended claims cover all such modifications and embodiments as fall within the true spirit and scope of the present invention.

What is claimed is:

1. A method of detecting a consensus motif in a multitude of data sequences without reference to any prior known motif, the method comprising the steps of:

obtaining the data sequences;

identifying potential signal (PS) segments of interest in the data sequences without reference to any prior known motif, wherein each of the PS segments comprises a sequence of positions, each of the positions has a character taken from a given alphabet, and each of the data sequences includes one or more of the PS segments;

carrying out comparison and alignment processes amongst the PS segments to extract the consensus motif, including the steps of selecting one of the PS segments from each of the data sequences, forming local alignments of the selected PS segments multiple times;

from each of the local alignments of the selected PS segments, obtaining a majority substring $s_m$, and using the majority substring to identify a putative consensus motif;

determining the number of times each of the putative consensus motifs occurs on the data sequences;

identifying one of the putative consensus motifs as the consensus motif based on said number of occurrences of each of the putative consensus motifs in the data sequences; and using one or more processing units, executing a consensus motif detection program, to perform the step of forming multiple local alignments of the selected PS segments.

2. A method according to claim 1, wherein the identifying step includes the step of using an unsupervised motif discovery process to identify the PS segments.

3. A method according to claim 2, wherein the step of using the unsupervised motif discovery process includes the steps of:

extracting all common motifs across the sequence using the unsupervised motif discovery process; and for each of at least selected positions in the sequence, computing the weighted sum of the common motifs that cover said position.

4. A method according to claim 3, wherein the identifying step includes the further step of identifying as the PS segments the positions where said weighted sum is above a given threshold.

5. A method according to claim 1, wherein the identifying the consensus motif includes:

selecting one of the putative consensus motifs as the consensus motif.

6. Apparatus for detecting a consensus motif in a multitude of data sequences without reference to any prior known motif, comprising:

at least one processing unit operative to (i) obtain the data sequences, (ii) identify potential signal (PS) segments of interest in the data sequences without reference to any prior known motif, and (iii) carry out comparison and alignment processes amongst the PS segments to extract the consensus motif, wherein each of the PS segments comprises a sequence of positions, each of the positions has a character taken from a given alphabet, and each of the data sequences includes one or more of the PS segments;

and wherein the comparison and alignment processes include selecting one of the PS segments from each of the data sequences, forming local alignments of the selected PS segments multiple times;

from each of the local alignments of the selected PS segments, obtaining a majority substring $s_m$, and using the majority substring to identify a putative consensus motif;

determining the number of times each of the putative consensus motifs occurs on the data sequences;

identifying one of the putative consensus motifs as the consensus motif based on said number of occurrences of each of the putative consensus motifs in the data sequences.

7. Apparatus according to claim 6, wherein the at least one processing unit is operative to use an unsupervised motif discovery process to identify the PS segments.

8. Apparatus according to claim 7, wherein the at least one processing unit is operative to use the unsupervised motif discovery process to extract all common motifs across the sequence using the unsupervised motif discovery process; and for each of at least selected positions in the sequence, to compute the weighted sum of the common motifs that cover said position.

9. Apparatus according to claim 8, wherein the at least one processing unit is operative to identify as the PS segments the positions where said weighted sums above a given threshold.

10. Apparatus according to claim 6, wherein the identifying the consensus motif includes selecting one of the putative consensus motifs as the consensus motif.

11. A program storage device readable by machine, tangibly embodying a program of instructions executable by the machine to perform method steps for detecting a consensus motif in a multitude of data sequences without reference to any prior known motif, the method steps comprising:

obtaining the data sequences;

identifying potential signal (PS) segments of interest in the data sequences without reference to any prior known motif, wherein each of the PS segments comprises a sequence of positions, each of the positions has a character taken from a given alphabet, and each of the data sequences includes one or more of the PS segments;

carrying out comparison and alignment processes amongst the PS segments to extract the consensus motif, including the steps of selecting one of the PS segments from each of the data sequences, forming local alignments of the selected PS segments multiple times;

from each of the local alignments of the selected PS segments, obtaining a majority substring $s_m$, and using the majority substring to identify a putative consensus motif;

determining the number of times each of the putative consensus motifs occurs on the data sequences;

identifying one of the putative consensus motifs as the consensus motif based on said number of occurrences of each of the putative consensus motifs in the data sequences.

12. A program storage device according to claim 11, wherein the identifying step includes the step of using an unsupervised motif discovery process to identify the PS segments.

13. A program storage device according to claim 12, wherein the step of using the unsupervised motif discovery process includes the steps of:

extracting all common motifs across the sequence using the unsupervised motif discovery process; and for each of at least selected positions in the sequence, computing the weighted sum of the common motifs that cover said position.

14. A program storage device according to claim 13, wherein the identifying step includes the further step of identifying as the PS segments the positions where said weighted sum is above a given threshold.

15. A program storage device according to claim 11, wherein the identifying the consensus motif includes selecting one of the putative consensus motifs as the consensus motif.

16. A method of detecting a consensus motif in a multitude of data sequences without reference to any prior known motif, the method comprising the steps of:

obtaining the data sequences;

identifying potential signal (PS) segments of interest in the data sequences without reference to any prior known motif, wherein each of the PS segments comprises a sequence of positions, each of the positions has a character taken from a given alphabet, and each of the data sequences includes one or more of the PS segments;

carrying out comparison and alignment processes amongst the PS segments to extract the consensus motif, including the steps of selecting one of the PS segments from each of the data sequences, forming local alignments of the selected PS segments multiple times;

from each the local alignments of the selected PS segments, computing a putative consensus motif;

determining the number of times each of the putative consensus motifs occurs on the data sequences;

identifying one of the putative consensus motifs as the consensus motif based on said number of occurrences of each of the putative consensus motifs in the data sequences;

using one or more processing units, executing a consensus motif detection program, to perform the step of forming multiple local alignments of the selected PS segments; and wherein:

each of the multiple alignments includes at least a plurality of the selected PS segments;

in each of the multiple alignments, each position in each of the PS segments in said each multiple alignment is aligned with one of the positions in each of the others of the PS segments in said each multiple alignment; and the identifying a putative consensus motif from each of the multiple alignments includes obtaining a majority substring $s_m$ from each of the multiple alignments by identifying a majority base at each of the aligned positions in said each of the multiple alignments.

17. The method according to claim 16, wherein the identifying the consensus motif includes scanning each of the data sequences for the occurrences of each of the $s_m$s with at most d error; and picking as the consensus motif the one of the $s_m$s having a best occurrence in the data sequences based on said scanning.

18. The method according to claim 1, wherein the identifying potential signal (PS) segments of interest includes:

extracting a multitude of common motifs across the sequences using an unsupervised motif discovery process;

for each of the positions in the data sequences, counting the number of the common motifs that cover said each position; and using the positions in the sequences with counts, of the number of the common motifs that cover the positions, above a defined level, as predictions of the PS segments.

19. The method according to claim 1, wherein:

each of the data sequences has a number of the PS segments;

the obtaining a majority substring from each of the multiple local alignments includes, from each of the multiple local alignments, identifying a majority base at each aligned position in said each of the of the multiple local alignments, and determining a score f as the sum total of the positions in the PS segments, in said each of the multiple local alignment, that agree with the majority substring obtained from said each of the multiple local alignments; and the putative consensus motifs are the majority substrings obtained from the multiple local alignments whose f score exceeds a given threshold.

* * * * *